(12) United States Patent
Beebe et al.

(10) Patent No.: US 8,603,416 B2
(45) Date of Patent: Dec. 10, 2013

(54) DEVICE FOR AND METHOD OF EXTRACTING A FRACTION FROM A BIOLOGICAL SAMPLE

(75) Inventors: David J. Beebe, Monona, WI (US); Scott M. Barry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 776 days.

(21) Appl. No.: 12/713,950

(22) Filed: Feb. 26, 2010

(65) Prior Publication Data
US 2011/0213133 A1   Sep. 1, 2011

(51) Int. Cl.
*B03C 1/02*   (2006.01)
(52) U.S. Cl.
USPC .......................................... 422/527; 422/501
(58) Field of Classification Search
USPC .......... 204/545, 557, 660, 560; 422/500, 501, 422/527
See application file for complete search history.

(56) References Cited

U.S. PATENT DOCUMENTS

| | | | |
|---|---|---|---|
| 5,279,936 A | 1/1994 | Vorpahl | |
| 6,117,398 A | 9/2000 | Bienhaus et al. | |
| 7,820,454 B2 | 10/2010 | Su et al. | |
| 8,017,340 B2 | 9/2011 | Collier et al. | |
| 8,048,633 B2 | 11/2011 | Collier et al. | |
| 2004/0224380 A1 | 11/2004 | Chou et al. | |
| 2005/0112601 A1 | 5/2005 | Hassibi et al. | |
| 2005/0208548 A1 | 9/2005 | Block et al. | |
| 2006/0024824 A1 | 2/2006 | Woodside et al. | |
| 2007/0042396 A1 | 2/2007 | Park et al. | |
| 2008/0124779 A1 | 5/2008 | Oh et al. | |
| 2008/0226500 A1 | 9/2008 | Shikida et al. | |
| 2009/0191594 A1* | 7/2009 | Ohashi .......................... 435/91.2 |
| 2009/0246782 A1 | 10/2009 | Kelso et al. | |
| 2010/0273142 A1 | 10/2010 | Prins et al. | |
| 2010/0291666 A1 | 11/2010 | Collier et al. | |

FOREIGN PATENT DOCUMENTS

WO   2006071770   7/2006

OTHER PUBLICATIONS

"Development of an enzymatic reaction device using magnetic bead-cluster handling", Shikida et al, J. Micromech. Microeng. 16 (2006) 1875-1883.
"Controlled microfluidic interfaces", Atencia et al, Nature, vol. 437, Sep. 29, 2005, 648-655.
"Using wettability and interfacial tension to handle droplets of magnetic beads in a micro-chemical-analysis system", Shikida et al, Sensors and Actuators B 113 (2006) 563-569.
"Droplet-based gene expression analysis using a device with magnetic force-based-droplet-handling system", Okochi et al, Journal of Bioscience and Bioengineering, vol. 109, No. 2, 2010, 193-197.
"On-chip polymerase chain reaction microdevice employing a magnetic droplet-manipulation system", Tsuchiya et al, Sensors and Actuators B 130 (2008) 583-588.
"Forced motion of a probe particle near the colloidal glass transition", Habdas et al, Europhys. Lett., 67(3), pp. 477-583 (2004).

* cited by examiner

*Primary Examiner* — Paul Hyun
(74) *Attorney, Agent, or Firm* — Boyle Fredrickson, S.C.

(57) ABSTRACT

A device and method are provided for facilitating extraction of a fraction from a biological sample. The biological sample includes non-desired material and a fraction-bound solid phase substrate. The device includes an input zone for receiving the biological sample therein and a phase-gate zone for receiving an isolation buffer therein. An output zone receives a reagent therein. A force is movable between a first position adjacent the input zone and a second position adjacent the output zone. The force urges the fraction-bound solid phase substrate from the input zone, through the phase-gate zone and into the output zone.

27 Claims, 3 Drawing Sheets

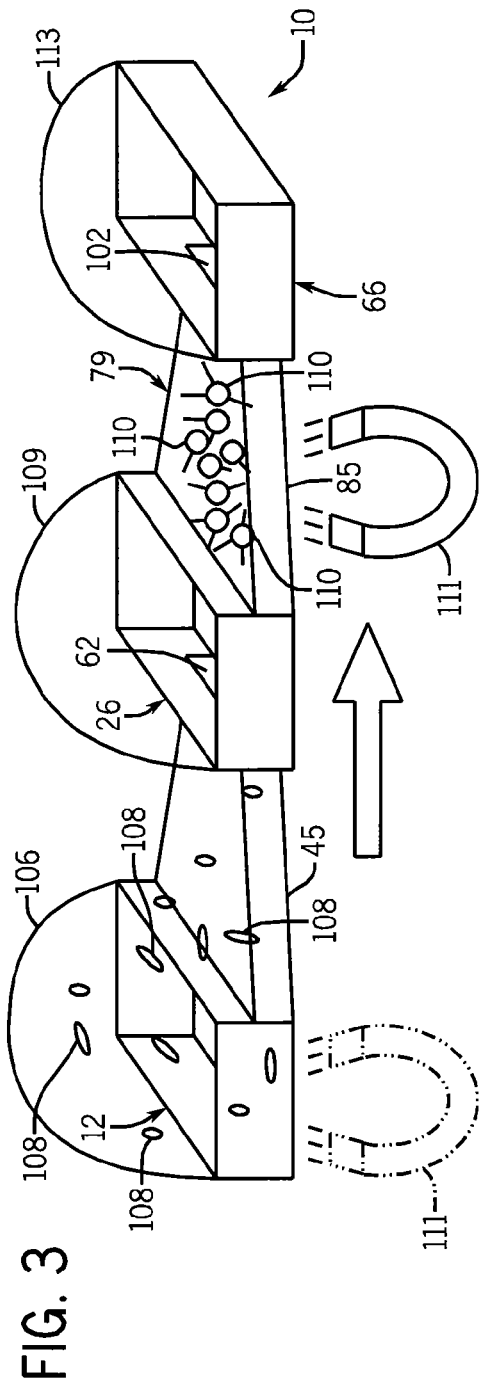
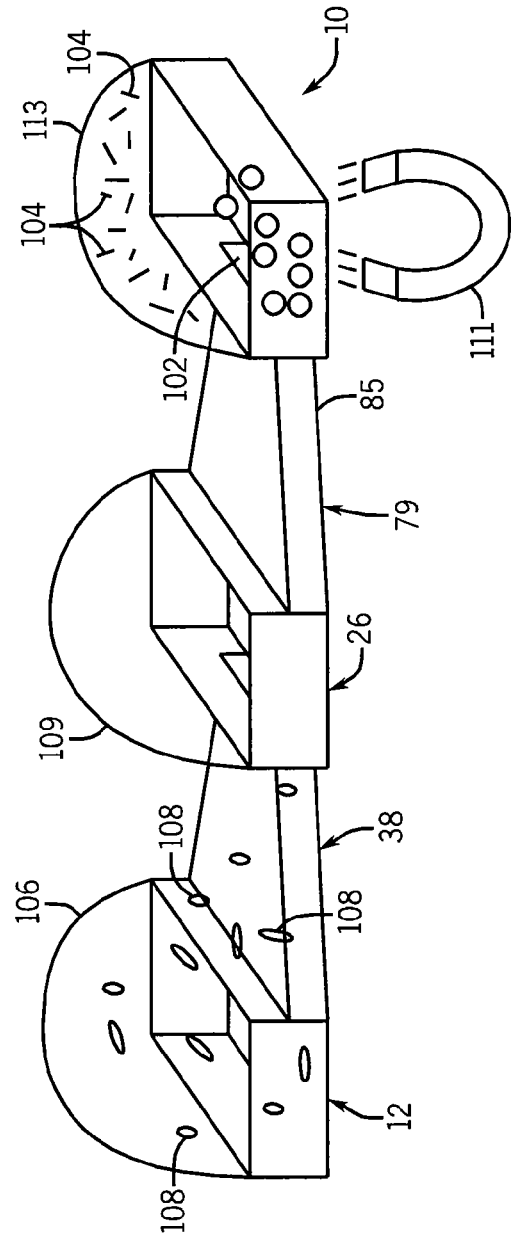

DEVICE FOR AND METHOD OF EXTRACTING A FRACTION FROM A BIOLOGICAL SAMPLE

REFERENCE TO GOVERNMENT GRANT

This invention was made with government support under W81XWH-08-1-0525 awarded by the ARMY/MRMC and CA104162 awarded by the National Institutes of Health. The government has certain rights in this invention.

FIELD OF THE INVENTION

The present invention relates generally to the extraction of nucleic acid and protein purification, and in particular, to a device for and a method of extracting a fraction from cultured cells, tissue samples and other biological materials.

BACKGROUND AND SUMMARY OF THE INVENTION

Effective isolation of nucleic acids from biological samples (e.g. cultured cells, tissue, viruses) is an essential prerequisite for efficient downstream amplification, detection, and quantification of specific genetic sequences via quantitative polymerase chain reaction (qPCR). The extraction process requires lysing the cells with harsh extraction reagents, such as detergents or enzymes, thereby resulting in a mixture of nucleic acids, cellular debris and extraction reagents. The nucleic acids are then separated/purified from the cellular debris and extraction reagents using a variety of techniques (e.g. organic solvent extraction, chromatography, centrifugation, dialysis). These techniques can be very time-consuming, tedious, and often require multiple washing steps. By way of example, commercially-available nucleic acid isolation kits require approximately 15 minutes to over one hour to complete, largely due to the multiple washing steps required to sufficiently separate the nucleic acids from the cellular debris and extraction reagents. Consequently, it has been suggested that as much as 15% of all molecular biology research time is devoted to purification.

In view of the foregoing, various attempts have been made to reduce the time associated with isolating nucleic acids from a biological sample. By way of example, Kelso, United States Patent Application No. 20090246782 discloses a system, device, and method for performing biological reactions. More specifically, the system contemplates placing a sample in a first chamber. The first chamber includes first processing reagents to generate a processed sample. The processed sample is moved through a water and alcohol immiscible, hydrophobic, or lipophilic barrier to a second chamber. The processed sample is treated in said second chamber with second processing reagents to generate a further processed sample.

While functional for its intended purpose, the system disclosed in the '782 application has certain limitations. For example, the reagents and immiscible phase of the system disclosed in the '782 application must be confined within corresponding chambers. As a result, the system requires the use of an external pump or two-axis magnet to move the processed sample between the chambers. It can be appreciated that the use of an external pump may have undesired effects on the sample. Alternatively, the use of a two-axis magnet may add unwanted cost and complexity to the system. In addition, the use of a plurality of chambers to isolate the nucleic acids from a biological sample may limit the throughput of the system.

Therefore, it is a primary object and feature of the present invention to provide a device for and a method of extracting and purifying a fraction from cultured cells, tissue samples and other biological materials.

It is a further object and feature of the present invention to provide a device for and a method of extracting and purifying a fraction from cultured cells, tissue samples and other biological materials that is simpler and more efficient than prior devices and methods.

It is a still further object and feature of the present invention to provide a device for and a method of extracting and purifying a fraction from cultured cells, tissue samples and other biological materials that has higher throughput than prior devices and methods.

In accordance with the present invention, a device is provided for facilitating extraction of a fraction from a biological sample. The biological sample includes non-desired material and a fraction-bound solid phase substrate. The device includes an input zone for receiving the biological sample therein and a phase-gate zone for receiving an isolation buffer therein. An output zone receives a reagent therein. A force is movable between a first position adjacent the input zone and a second position adjacent the output zone. The force urges the fraction-bound solid phase substrate from the input zone, through the phase-gate zone and into the output zone.

It is contemplated for the isolation buffer to be an oil. The oil prevents the non-desired material from passing therethrough. The device further includes a first channel has an input in communicating with the input zone and an output communicating with the phase-gate zone. The input of the first channel is larger than the output of the first channel. The first channel is partial defined by first and second sidewalls. The first and second sidewalls converge from the input of the first channel to the output of the first channel. In addition, the device may include a second channel having an input in communicating with the phase-gate zone and an output communicating with the output zone. The input of the second channel is larger than the output of the second channel and the input of the first channel is larger than the output of the first channel. The second channel is partial defined by first and second sidewalls. The first and second sidewalls defining the second channel converge from the input of the second channel to the output of the second channel.

In accordance with a further aspect of the present invention, a device is provided for facilitating extraction of a fraction from a biological sample. The biological sample includes non-desired material and a fraction-bound solid phase substrate. The device includes an input zone for receiving the biological sample therein and an output zone for receiving a reagent therein. A pathway interconnects the input zone and the output zone. A force field is movable between a first position adjacent the input zone and a second position adjacent the output zone. The force urges the fraction-bound solid phase substrate from the input zone, through the pathway and into the output zone.

An isolation buffer is disposed in the pathway. The isolation buffer prevents the non-desired material from passing therethrough. The pathway includes a phase-gate zone for housing the isolation buffer. The pathway is at least partially defined by a first channel has an input in communicating with the input zone and an output communicating with the phase-gate zone. The input of the first channel is larger than the output of the first channel. The first channel is partially defined by first and second sidewalls. The first and second sidewalls converge from the input of the first channel to the output of the first channel. The pathway may be further defined by a second channel having an input in communicating with the phase-gate zone and an output communicating with the output zone. The input of the second channel is larger than the output of the second channel. The second channel is partially defined by first and second sidewalls. The first and second sidewalls converge from the input of the second channel to the output of the second channel.

In accordance with a still further aspect of the present invention, a method is provided for facilitating extraction of a fraction from a biological sample. The biological sample includes non-desired material and a fraction-bound solid phase substrate. The method includes the steps of depositing the biological sample in an input zone and drawing the fraction-bound phase substrate from the input zone, through a phase-gate zone and into the output zone with a force.

The phase-gate zone includes an isolation buffer that prevents the non-desired material from passing therethrough. The isolation buffer may be an oil. The method may include the additional step of interconnecting the input zone and the phase-gate zone with a channel having an input in communication with the input zone and an output in communication with the phase-gate zone. The input of the channel is larger than the output of the channel. In addition, the phase-gate zone and the output zone may be interconnected with a channel having an input in communication with the phase-gate zone and an output in communication with the output zone. The input of the channel is larger than the output of the channel.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 1 is an isometric view of a device in accordance with the present invention in an initial configuration;

FIG. 2 is a cross-sectional view of the device of the present invention taken along line 2-2 of FIG. 1;

FIG. 3 is an isometric view of a device of the present invention in a second configuration;

FIG. 4 is an isometric view of a device of the present invention in a third configuration;

DETAILED DESCRIPTION OF THE DRAWINGS

Figures 1, 2:
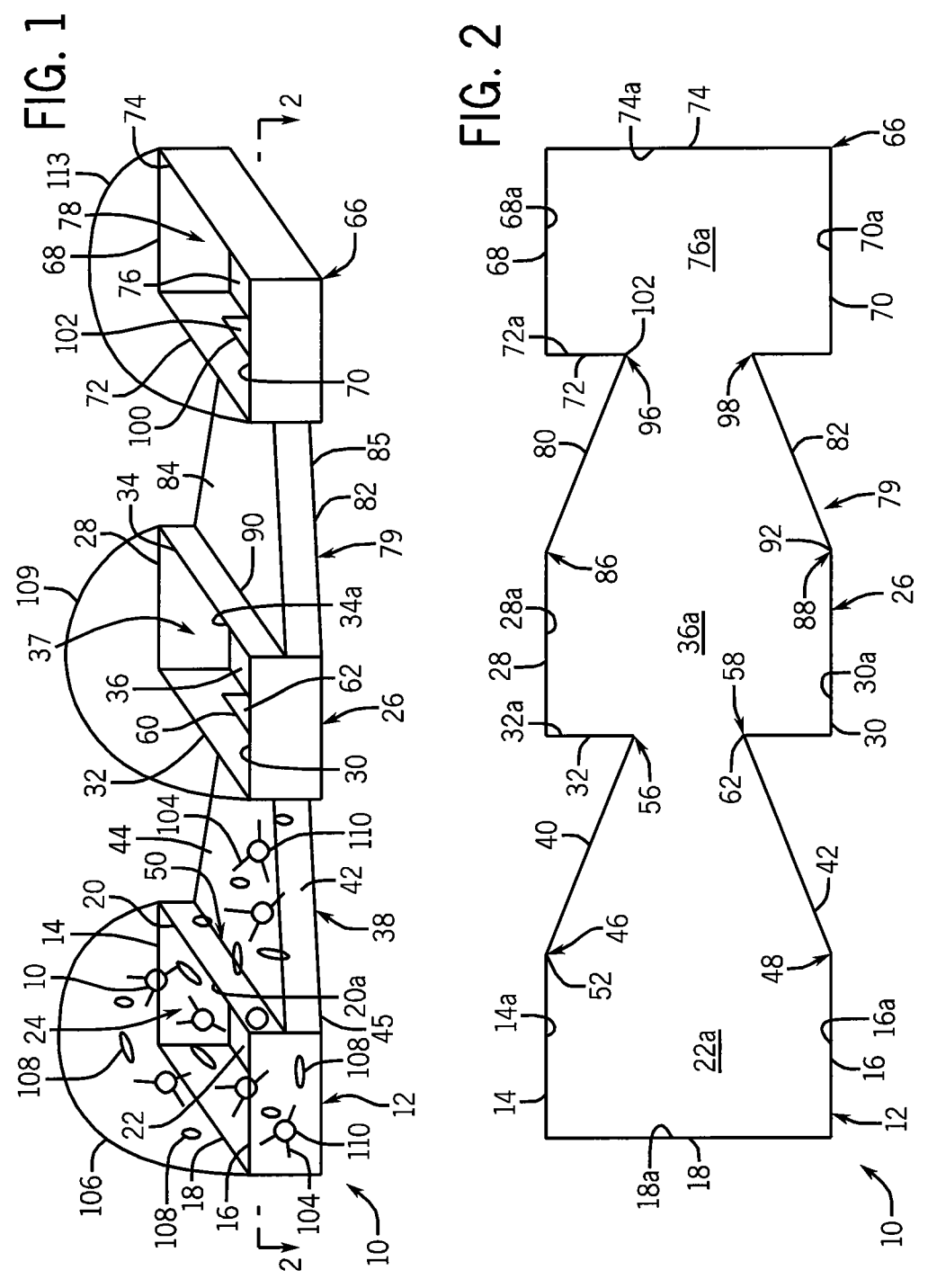
Figure 5:
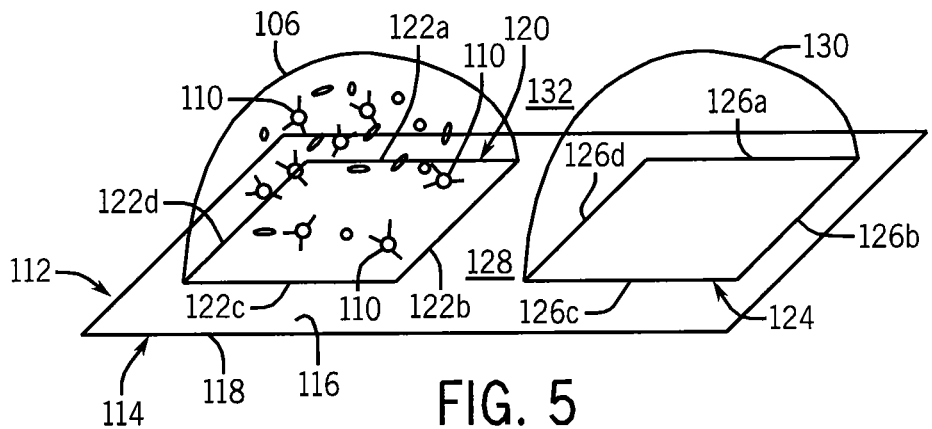
FIG. 5 is an isometric view of an alternate embodiment of a device in accordance with the present invention in an initial configuration.

Referring to FIGS. 1-4, a device for extracting and purifying a fraction from cultured cells, tissue samples and other biological materials in accordance with the present invention is generally designated by the reference numeral 10. Device 10 includes input zone or well 12 defined by first and second sidewalls 14 and 16, respectively, first and second end walls 18 and 20, respectively, and bottom wall 22. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a biological sample therein, as hereinafter described. While input well 12 has a generally rectangular configuration in the depicted embodiment, other configurations are contemplated without deviating from the scope of the present invention.

Device 10 further includes phase-gate zone or well 26 downstream of input well 12 and being defined by first and second sidewalls 28 and 30, respectively, upstream wall 32, downstream wall 34 and bottom wall 36. Inner surfaces 28a and 30a of sidewalls 28 and 30, respectively, inner surface 32a of upstream wall 32, inner surface 34a of downstream wall 34, and upper surface 36a of bottom wall 36 define phase-gate cavity 37 for receiving an isolation buffer therein, as hereinafter described. Again, although phase-gate well 26 has a generally rectangular configuration in the depicted embodiment, other configurations are contemplated without deviating from the scope of the present invention.

Input well 12 and phase-gate well 26 are interconnected by first channel 38. First channel 38 extends along an axis and is defined by first and second sidewalls 40 and 42, respectively, upper wall 44 and bottom wall 45. Input ends 46 and 48 of first and second sidewalls 40 and 42, respectively, of first channel 38 and input end 50 of upper wall 44 of input channel 38 intersect end wall 20 of input well 12 so as to define input 52 to first channel 38. Output ends 56 and 58 of first and second sidewalls 40 and 42, respectively, of first channel 38 and output end 60 of upper wall 44 of first channel 38 intersect upstream wall 32 of phase-gate well 26 so as to define output 62 of first channel 38. Bottom wall 45 of first channel 38 is generally co-planar with bottom walls 22 and 36 of input well 12 and phase-gate well 26, respectively. As best seen in FIG. 2, first and second sidewalls 40 and 42, respectively, of first channel 38 converge towards each other from input 52 to output 62, for reasons hereinafter described.

Device 10 further includes output zone or well 66 downstream of phase-gate well 26 and being defined by first and second sidewalls 68 and 70, respectively, upstream wall 72, downstream wall 74 and bottom wall 76. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a reagent therein, as hereinafter described. Again, output well 66 has a generally rectangular configuration in the depicted embodiment, other configurations are contemplated without deviating from the scope of the present invention.

Output well 66 and phase-gate well 26 are interconnected by second channel 79. Second channel 79 extends along an axis and is defined by first and second sidewalls 80 and 82, respectively, upper wall 84 and bottom wall 85. Input ends 86 and 88 of first and second sidewalls 80 and 82, respectively, of second channel 79 and input end 90 of upper wall 84 of second channel 79 intersect downstream wall 34 of phase-gate well 26 so as to define input 92 to second channel 79. Output ends 96 and 98 of first and second sidewalls 80 and 82, respectively, of second channel 79 and output end 100 of upper wall 84 of second channel 79 intersect upstream wall 72 of output well 66 so as to define output 102 of second channel 79. Bottom wall 76 of second channel 79 is generally co-planar with bottom walls 36 and 76 of phase-gate well 26 and output well 66, respectively. As best seen in FIG. 2, first and second sidewalls 80 and 82, respectively, of second channel 79 converge towards each other from input 92 to output 102, for reasons hereinafter described.

In operation, it is intended to utilize device 10 to extract fraction 104, such as nucleic acids, whole cells and/or proteins, from biological sample 106. As is known, biological sample 106 may include non-desired material 108 such as lysate, bodily fluids, forensic samples, and/or biological contaminations. In order to prepare biological sample 106 for extraction of fraction 104, an appropriate reagent is added to biological sample 106 and mixed such that fraction 104 binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as gravity, ultrasonic actuation or the like are contemplated as beng within the scope of the present invention. Once mixed with the reagent, biological sample 106 is deposited in input cavity 24 of input well 12; isolation buffer 109, such as oil or wax, is deposited in phase-gate cavity 37 of phase-gate well 26; and a desired reagent 113 is deposited in output cavity 78 of output well 66. It can be appreciated that the mixing of biological sample 106 and the reagent may occur in input cavity 24 of input well 12 and/or first channel 38 without deviating from the scope of the present invention.

It is noted that the cross-sectional area of input 52 to first channel 38 is greater than the cross-sectional area of output 62 of first channel 38. As a result, biological sample 106 flows into first channel 38 through input 52 thereof. However, the surface tension of isolation buffer 109 in phase-gate cavity 37 of phase-gate well 26 at output 62 of first channel 38 prevents biological sample 106 from flowing into phase-gate cavity 37 of phase-gate well 26 through output 62 of first channel 38. Likewise, the surface tension of reagent 113 in output cavity 78 of output well 66 at output 102 of second channel 79 prevents isolation buffer 109 from flowing into output cavity 78 of output well 66 at output 102 of second channel 79.

In order to extract fraction-bound solid phase substrate 110 from biological sample 106, a force to which the solid phase substrate is attracted is positioned adjacent, and preferably below, input well 12. As heretofore described, it is contemplated for the solid phase substrate to be a paramagnetic material attracted to a corresponding magnetic field. As such, in order to generate the magnetic field, magnet 111 is positioned below input well 12 such that fraction-bound solid phase substrate 110 is magnetically attracted thereto. Magnet 111 is sequentially moved: 1) below bottom wall 45 of first channel 38 such that fraction-bound solid phase substrate 110 are drawn into first channel 38 through input 52 thereof; 2) below bottom wall 36 of phase-gate well 26 such that fraction-bound solid phase substrate 110 are drawn into phase-gate well 26 through output 62 of first channel 38; 3) below bottom wall 85 of second channel 79 such that fraction-bound solid phase substrate 110 are drawn into second channel 79 through input 92 thereof, FIG. 3; and 4) below bottom wall 76 of output well 66 such that fraction-bound solid phase substrate 110 are drawn into output well 66 through output 102 of second channel 79, FIG. 4. It is intended to move magnet 111 from its initial position below input well 12 to a position below output well 66 in less than 10 seconds. However, other time periods are contemplated as being within the scope of the present invention.

As previously noted, the surface tension of isolation buffer 109 in phase-gate cavity 37 of phase-gate well 26 at output 62 of first channel 38 prevents biological sample 106 from flowing into phase-gate cavity 37 of phase-gate well 26 through output 62 of first channel 38 and the surface tension of reagent 113 in output cavity 78 of output well 66 at output 102 of second channel 79 prevents isolation buffer 109 from flowing into output cavity 78 of output well 66 at output 102 of second channel 79. It can be appreciated that as fraction-bound solid phase substrate 110 passes through phase-gate well 26 and second channel 79, fraction-bound solid phase substrate 110 are washed by isolation buffer 109 therein, thereby effectively isolating fraction-bound solid phase substrate 110 from the remainder of biological sample 106. With fraction-bound solid phase substrate 110 isolated from the remainder of biological sample 106 in output well 66, fraction-bound solid phase substrate 110 may be treated in output well 66 by reagent 113 contained therein as desired by a user. In addition, it can be appreciated that output well 66 may be operatively connected to additional downstream components for further processing of fraction-bound solid phase substrate 110.

As described, the methodology of the present invention does not require any electronic equipment such as centrifuges, rockers/shakers, or incubators, while consuming only minimal volumes of reagents in the three wells. It can also be appreciated that the simplicity of device 10 allows for it to be easily reconfigured to form a mating relationship with the input/output requirements of upstream and downstream components.

Figure 6:
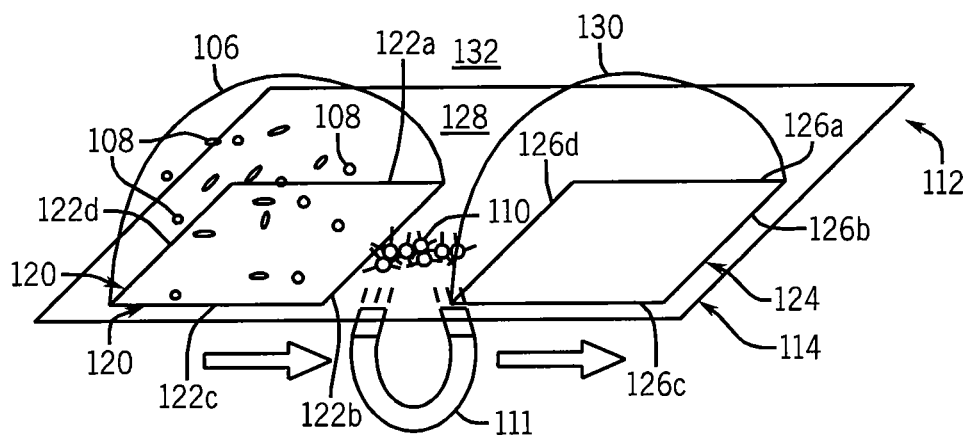
FIG. 6 is an isometric view of the alternate embodiment of the device in accordance with the present invention in a second configuration.

Referring to FIGS. 5-6, an alternate embodiment of the device for extracting and purifying a fraction from cultured cells, tissue samples and other biological materials in accordance with the present invention is generally designated by the reference numeral 112. Device 112 includes plate 114 having upper and lower surfaces 116 and 118, respectively. Except as hereinafter described, upper surface 116 of plate 114 is hydrophobic. Upper surface 116 of plate 114 includes a hydrophilic input zone 120 defined by edges 122a-122d such that input zone 120 has a generally square configuration. However, other configurations are contemplated as being within the scope of the present invention. In addition, upper surface 116 of plate 114 includes a hydrophilic output zone 124 defined by edges 126a-126d such that output zone 124 has a generally square configuration. However, other configurations are contemplated as being within the scope of the present invention. The portion of upper surface 116 of plate 114 outside of input zone 120 and output zone 124 defines hydrophobic isolation zone 128.

In operation, the mixture of biological sample 106 and a reagent, as heretofore described, is deposited on input zone 120 and a desired reagent 130 is deposited on output zone 124. Device 112 is flooded with isolation buffer 132 (e.g. oil, wax or the like) such that the mixture biological sample 106 and the reagent deposited on input zone 120 and desired reagent 130 deposited on output zone 124 are completely submerged in isolation buffer 132.

In order to extract fraction-bound solid phase substrate 110 from biological sample 106, a force to which the solid phase substrate of fraction-bound solid phase substrate 110 is attracted is positioned adjacent, and preferably below, input zone 120. In the exemplary embodiment, it is contemplated for the solid phase substrate of fraction-bound solid phase substrate 110 to be a paramagnetic material attracted to a corresponding magnetic field. As such, in order to generate the magnetic field, magnet 111 is positioned below input zone 120 such that fraction-bound solid phase substrate 110 is magnetically attracted thereto. Referring to FIG. 6, magnet 111 is sequentially moved: 1) below isolation zone 128 such that fraction-bound solid phase substrate 110 are drawn into isolation buffer 132; and 2) below output zone 124 such that fraction-bound solid phase substrate 110 are drawn into reagent 130.

It is noted that the surface tension of isolation buffer 132 deposited on isolation zone 128 prevents biological sample 106 flowing from input zone 120 into isolation zone 126. In addition, the surface tension of reagent 130 deposited on output zone 124 prevents isolation buffer 132 from flowing into output zone 124. It can be appreciated that as fraction-bound solid phase substrate 110 passes through isolation buffer 132 deposited on isolation zone 128, fraction-bound solid phase substrate 110 are washed by isolation buffer 132, thereby effectively isolating fraction-bound solid phase substrate 110 from the remainder of biological sample 106. With fraction-bound solid phase substrate 110 isolated from the remainder of biological sample 106 in reagent 130 deposited on output zone 124, fraction-bound solid phase substrate 110 may be acted on by reagent 130. In addition, it can be appreciated that reagent 130 may be operatively connected to additional downstream components for further processing of fraction-bound solid phase substrate 110.

Figure 7:
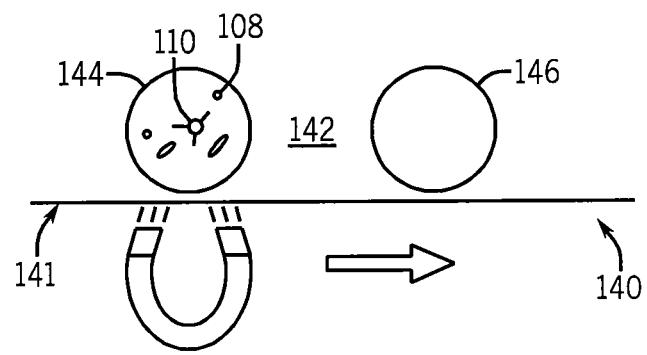
FIG. 7 is a schematic view of a still further embodiment of a device in accordance with the present invention in an initial configuration.

Referring to FIG. 7, a still further embodiment of a device for extracting and purifying a fraction from cultured cells, tissue samples and other biological materials in accordance with the present invention is generally designated by the reference numeral 140. Device 140 includes chamber 141 adapted for receiving isolation buffer 142 therein. Drop 144 of the mixture of biological sample 106 and a reagent, as heretofore described, is deposited in isolation buffer 142 so as to define an input zone. In addition, drop 146 of a desired reagent is deposited in isolation buffer 142 so as to define an output zone.

In order to extract fraction-bound solid phase substrate 110 from biological sample 106, a force to which the solid phase substrate of fraction-bound solid phase substrate 110 is attracted is positioned adjacent drop 144. In the exemplary embodiment, it is contemplated for the solid phase substrate of fraction-bound solid phase substrate 110 to be a paramagnetic material attracted to a corresponding magnetic field. As such, in order to generate the magnetic field, magnet 111 is positioned adjacent drop 144 such that fraction-bound solid phase substrate 110 is magnetically attracted thereto. Magnet 111 is moved from a position adjacent drop 144 to a position adjacent, drop 146 such that fraction-bound solid phase substrate 110 are sequentially drawn: 1) into isolation buffer 142; and 2) into drop 146.

It is noted that the surface tension of isolation buffer 142 prevents biological sample 106 from passing out of drop 144 into isolation buffer 142. In addition, the surface tension of drop 146 prevents isolation buffer 142 from flowing into drop 146. It can be appreciated that as fraction-bound solid phase substrate 110 passes through isolation buffer 142, fraction-bound solid phase substrate 110 are washed by isolation buffer 142, thereby effectively isolating fraction-bound solid phase substrate 110 from the remainder of biological sample 106. With fraction-bound solid phase substrate 110 isolated from the remainder of biological sample 106, fraction-bound solid phase substrate 110 may be acted on by the reagent of drop 144. In addition, it can be appreciated that drop 144 may be operatively connected to additional downstream components for further processing of fraction-bound solid phase substrate 110.

Various modes of carrying out the invention are contemplated as being within the scope of the following claims particularly pointing out and distinctly claiming the subject matter, which is regarded as the invention.

We claim:

1. A device for facilitating extraction of a fraction from a biological sample, the biological sample including non-desired material and a fraction-bound solid phase substrate, the device comprising:
   an input zone for receiving the biological sample therein;
   a phase-gate zone for receiving an isolation buffer therein;
   an output zone for receiving a reagent therein;
   a first channel having an input in communication with the input zone and an output communicating with the phase-gate zone, the input of the first channel being larger than the output of the first channel; and
   a force movable between a first position adjacent the input zone and a second position adjacent the output zone;
   wherein the force urges the fraction-bound solid phase substrate from the input zone, through the phase-gate zone and into the output zone.

2. The device of claim 1 wherein the isolation buffer is an oil, the oil preventing the non-desired material from passing therethrough.

3. The device of claim 1 further comprising a plate having an upper surface, the upper surface including:
   first hydrophilic portion communicating with the biological sample;
   a second hydrophilic portion communicating with the reagent; and
   a hydrophobic portion communicating with the isolation buffer.

4. A device for facilitating extraction of a fraction from a biological sample, the biological sample including non-desired material and a fraction-bound solid phase substrate, the device comprising:
   an input zone for receiving the biological sample therein;
   an output zone for receiving a reagent therein;
   a pathway interconnecting the input zone and the output zone;
   an isolation buffer disposed in the pathway, the isolation buffer preventing the non-desired material from passing therethrough; and
   a force field movable between a first position adjacent the input zone and a second position adjacent the input zone and the output zone;
   wherein:
   the force urges the fraction-bound solid phase substrate from the input zone, through the pathway and into the output zone;
   the pathway includes a phase-gate zone housing the isolation buffer and is at least partially defined by a first channel having an input in communication with the input zone and an output communicating with the phase-gate zone; and
   the input of the first channel is larger than the output of the first channel.

5. A device for facilitating extraction of a fraction from a biological sample, the biological sample including non-desired material and a fraction-bound solid phase substrate, the device comprising:
   an input zone for receiving the biological sample therein;
   a phase-gate zone for receiving an isolation buffer therein;
   an output zone for receiving a reagent therein;
   a plate having an upper surface, the upper surface including:
     a first hydrophilic portion communicating with the input zone;
     a second hydrophilic portion communicating with the output zone; and
     a hydrophobic portion communicating with the phase-gate zone; and
   a force movable between a first position adjacent the input zone and a second position adjacent the output zone;
   wherein the force urges the fraction-bound solid phase substrate from the input zone, through the phase-gate zone and into the output zone.

6. The device of claim 5 further comprising a first channel having an input in communication with the input zone and an output communicating with the phase-gate zone.

7. The device of claim 6 wherein the first channel is partially defined by first and second sidewalls, the first and second sidewalls converging from the input of the first channel to the output of the first channel.

8. The device of claim 6 further comprising a second channel having an input in communication with the phase-gate zone and an output communicating with the output zone.

9. The device of claim 8 wherein the input of the second channel is larger than the output of the second channel.

10. The device of claim 8 wherein the second channel is partially defined by first and second sidewalls, the first and second sidewalls converging from the input of the second channel to the output of the second channel.

11. A device for facilitating extraction of a fraction from a biological sample, the biological sample including non-desired material and a fraction-bound solid phase substrate, the device comprising:
   an input zone for receiving the biological sample therein;
   a phase-gate zone for receiving an isolation buffer therein;
   an output zone for receiving a reagent therein;
   a first channel having an input in communication with the input zone and an output communicating with the phase-gate zone; and
   a force movable between a first position adjacent the input zone and a second position adjacent the output zone;
   wherein:
   the force urges the fraction-bound solid phase substrate from the input zone, through the phase-gate zone and into the output zone;
   the input of the first channel is larger than the output of the first channel; and
   the first channel is partially defined by first and second sidewalls, the first and second sidewalls converging from the input of the first channel to the output of the first channel.

12. A device for facilitating extraction of a fraction from a biological sample, the biological sample including non-desired material and a fraction-bound solid phase substrate, the device comprising:
   an input zone for receiving the biological sample therein;
   a phase-gate zone for receiving an isolation buffer therein;
   an output zone for receiving a reagent therein;
   a first channel having an input in communication with the input zone and an output communicating with the phase-gate zone;
   a second channel having an input in communication with the phase-gate zone and an output communicating with the output zone, the input of the second channel being larger than the output of the second channel; and
   a force movable between a first position adjacent the input zone and a second position adjacent the output zone;
   wherein the force urges the fraction-bound solid phase substrate from the input zone, through the phase-gate zone and into the output zone.

13. The device of claim 12 wherein the input of the first channel is larger than the output of the first channel.

14. A device for facilitating extraction of a fraction from a biological sample, the biological sample including non-desired material and a fraction-bound solid phase substrate, the device comprising:
   an input zone for receiving the biological sample therein;
   a phase-gate zone for receiving an isolation buffer therein;
   an output zone for receiving a reagent therein;
   a first channel having an input in communication with the input zone and an output communicating with the phase-gate zone;
   a second channel having an input in communication with the phase-gate zone and an output communicating with the output zone; and
   a force movable between a first position adjacent the input zone and a second position adjacent the output zone;
   wherein;
   the force urges the fraction-bound solid, phase substrate from the input zone, through the phase-gate zone and into the output zone; and
   the second channel is partially defined by first and second sidewalls, the first and second sidewalls converging from the input of the second channel to the output of the second channel.

15. A device for facilitating extraction of a fraction from a biological sample, the biological sample including non-desired material and a fraction-bound solid phase substrate, the device comprising:
   an input zone for receiving the biological sample therein;
   an output zone for receiving a reagent therein;
   a pathway interconnecting the input zone and the output zone;
   an isolation buffer disposed in the pathway, the isolation buffer preventing the non-desired material froth passing therethrough; and
   a force field movable between a first position adjacent the input zone and second position adjacent the output zone;
   wherein:
   the force urges the fraction-bound solid phase substrate from the input zone, through the pathway and into the output zone;
   the pathway includes a phase-gate zone housing the isolation buffer and is at least partially defined by a first channel having an input in communication with the input zone and an output communicating with the phase-gate zone; and
   the pathway is further defined by a second channel having an input in communication with the phase-gate zone and an output communicating with the output zone, the input of the second channel being larger than the output of the second channel.

16. A device for facilitating extraction of a fraction from a biological sample, the biological sample including non-desired material and a fraction-bound solid phase substrate, the device comprising:
   an input zone for receiving the biological sample therein;
   an output zone for receiving a reagent therein;
   a pathway interconnecting the input zone and the output zone;
   an isolation buffer disposed in the pathway, the isolation buffer preventing the non-desired material from passing therethrough; and
   a force field movable between a first position adjacent the input zone and a second position adjacent the output zone;
   wherein:
   the force urges the fraction-bound solid phase substrate from the input zone, through the pathway and into the output zone;
   the pathway includes a phase-gate zone housing the isolation buffer and is at least partially defined by a first channel having an input in communication with the input zone and an output communicating with the phase-gate zone;

the pathway is further defined by a second channel having an input in communication with the phase-gate zone and an output communicating with the output zone; and the second channel is partially defined by first and second sidewalls, the first and second sidewalls converging from the input of the second channel to the output of the second channel.

17. A device for facilitating extraction of a fraction from a biological sample, the biological sample including non-desired material and a fraction-bound solid phase substrate, the device comprising:

an input zone for receiving the biological sample therein;
an output zone for receiving a reagent therein;
a pathway interconnecting the input zone and the output zone;
an isolation buffer disposed in the pathway, the isolation buffer preventing the non-desired material from passing therethrough; and
a force field movable between a first position adjacent the input zone and a second position adjacent the output zone;

wherein:
the force urges the fraction-bound solid phase substrate from the input zone, through the pathway and into the output zone;
the pathway-includes a phase-gate: zone housing the isolation buffer and is at least partially defined by a first channel having an input in communication with the input zone and an output communicating with the phase-gate zone; and
the first channel is partially defined by first and second sidewalls, the first and second sidewalls converging from the input of flue first channel to the output of the first channel.

18. A device for facilitating extraction of a fraction from a biological sample, the biological sample including non-desired material and a fraction-bound solid phase substrate, the device comprising:

an input zone for receiving the biological sample therein;
an output zone for receiving a reagent therein;
a pathway interconnecting the input zone and the output zone;
a plate having an upper surface, the upper surface including:
a first hydrophilic portion communicating with the input zone;
a second hydrophilic portion communicating with the output zone; and
a hydrophobic portion partially defining the pathway; and
a force field movable between a first position adjacent the input zone and a second position adjacent the output zone;
wherein the force urges the fraction-bound solid phase substrate from the input zone, through the pathway and into the output zone.

19. The device of claim 18 further comprising an isolation buffer disposed in the pathway, the isolation buffer preventing the non-desired material from passing therethrough.

20. The device of claim 19 wherein the pathway includes a phase-gate zone housing the isolation buffer.

21. The device of claim 20 wherein the pathway is at least partially defined by a first channel having an input in communication with the input zone and an output communicating with the phase-gate zone.

22. The device of claim 21 wherein the input of the first channel is larger than the output of the first channel.

23. The device of claim 21 wherein the first channel is partially defined by first and second sidewalls, the first and second sidewalls converging from the input of the first channel to the output of the first channel.

24. The device of claim 21 wherein the pathway is further defined by a second channel having an input in communication with the phase-gate zone and an output communicating with the output zone.

25. The device of claim 24 wherein the input of the second channel is larger than the output of the second channel.

26. The device of claim 25 wherein the input of the first channel is larger than the output of the first channel.

27. The device of claim 24 wherein the second channel is partially defined by first and second sidewalls, the first and second sidewalk converging from the input of the second channel to the output of the second channel.

* * * * *